(12) United States Patent
Hayman (10) Patent No.: US 10,379,024 B2
(45) Date of Patent: Aug. 13, 2019

(54) POISSON ENSEMBLE INVERSION

(71) Applicant: University Corporation for Atmospheric Research, Boulder, CO (US)

(72) Inventor: Matthew Hayman, Boulder, CO (US)

(73) Assignee: University Corporation for Atmospheric Research, Boulder, CO (US)

( * ) Notice: Subject to any disclaimer, the term of this patent is extended or adjusted under 35 U.S.C. 154(b) by 446 days.

(21) Appl. No.: 14/661,781

(22) Filed: Mar. 18, 2015

(65) Prior Publication Data

US 2016/0274016 A1    Sep. 22, 2016

(51) Int. Cl.
*G01N 15/02* (2006.01)
*G06F 17/18* (2006.01)
*G01N 15/00* (2006.01)

(52) U.S. Cl.
CPC ......... *G01N 15/0205* (2013.01); *G06F 17/18* (2013.01); *G01N 2015/0046* (2013.01)

(58) Field of Classification Search
CPC ........ G01N 15/0205; G01N 2015/0046; G06F 17/18; H04Q 3/00
USPC .......... 702/24; 1/1; 356/336, 519, 342, 28.5; 600/425
See application file for complete search history.

(56) References Cited

U.S. PATENT DOCUMENTS

| 5,856,865 | A  | * | 1/1999 | Galtier | G01P 5/26 |
| | | | | | 324/76.19 |
| 6,119,510 | A  | * | 9/2000 | Carasso | G01N 15/0205 |
| | | | | | 356/437 |
| 9,354,308 | B1 | * | 5/2016 | Conquest | G01S 13/9023 |
| 9,383,478 | B2 | * | 7/2016 | Miller | G01W 1/18 |
| 2006/0262324 | A1 | * | 11/2006 | Hays | G01N 21/47 |
| | | | | | 356/519 |
| 2009/0219529 | A1 | * | 9/2009 | Dietrich | G01N 15/1429 |
| | | | | | 356/335 |
| 2011/0019188 | A1 | * | 1/2011 | Ray | B64D 15/20 |
| | | | | | 356/342 |
| 2013/0314694 | A1 | * | 11/2013 | Tchoryk, Jr. | G01S 17/95 |
| | | | | | 356/28.5 |
| 2015/0182136 | A1 | * | 7/2015 | Durduran | G01B 9/02094 |
| | | | | | 600/425 |
| 2016/0202164 | A1 | * | 7/2016 | Trainer | G01N 15/0211 |
| | | | | | 356/336 |

FOREIGN PATENT DOCUMENTS

JP    2006113042 A  *  4/2006  ............. G01N 15/02

* cited by examiner

*Primary Examiner* — Mohammed Shamsuzzaman
(74) *Attorney, Agent, or Firm* — The Ollila Law Group LLC (57) ABSTRACT

A method for determining a distribution of events, a method for determining a distribution of particle sizes in a sample of air, and an apparatus for performing the same are provided. The method includes obtaining a measured ensemble property distribution function for one or more events, generating one or more theoretical ensemble property distribution functions based on Poisson statistics using one or more model parameters, and determining an event parameter property distribution function by fitting one or more of the theoretical ensemble property distribution functions to the measured ensemble property distribution function using a forward inversion algorithm.

9 Claims, 6 Drawing Sheets

POISSON ENSEMBLE INVERSION

GOVERNMENT LICENSE RIGHTS

The U.S. Government has a paid-up license in this invention and the right in limited circumstances to require the patent owner to license others on reasonable terms as provided for by the terms of Agreement No. AGS-0753581 awarded via joint National Science Foundation and National Center for Atmospheric Research cooperative agreement.

TECHNICAL FIELD

The present Application is directed towards ensemble measurements, and more particularly to deriving distributions of properties from ensemble measurements.

BACKGROUND OF THE INVENTION

The sizes of atmospheric particles and aerosols is important information in the atmospheric sciences. For example, the size of cloud vapor droplets, ice crystals, and aerosols are often needed to determine the properties and physics of thunderstorms. Data regarding atmospheric particle sizes is often collected from airborne instruments.

In previous measurement systems, particle size distributions have been estimated by measuring the sizes of individual particles. Once a sufficient number of particles are characterized, a histogram representing a particle size distribution is generated. This is problematic, however, because a large numbers of individual particle measurements are required. Acquiring the data needed to create a meaningful particle size histogram takes time and sometimes requires a long flight path for an airborne instrument, introducing potential errors into the data. Determining the sizes of individual particles is also a resource-intense activity that requires intensive real time processing capabilities to transmit, store, and process the required signals.

Previous particle measuring systems rely heavily on scattering models that make fundamental assumptions about particle properties such as the shape of a particle in making estimations. Moreover, the fundamental data unit that these systems approximate, individual particle size, is not useful; it is the distribution of particle sizes that is most important in the atmospheric sciences.

For example, forward scattering spectrometer technology is often used to estimate particle sizes. Mounted on the wing of an aircraft, forward scattering spectrometers focus laser light in the free stream outside the aircraft. Using a very small sample volume to avoid detecting more than one particle at a time, and assuming that particles are spherical in size, particle size is estimated based on the amount of forward scattered light. However, the error in particle size estimated increases substantially when particles are greater than 50 um in diameter, because the forward scattering spectrometer probe becomes sensitive to slight deviations in the probe's optical properties. Moreover, the forward scattering technique cannot be effectively applied to non-spherical particles because it is impossible to know what particle shape properties should be used. There is further uncertainty in sample volume because the sample volume of the probes is controlled using a focused laser and aperturing on the detector side, and this contributes to further error.

Optical array probes (OAP) are also frequently used to estimate particle sizes. Using a linear array of photo diodes illuminated by a laser, OAP form shadow images of particles. As a particle passes through the laser, it shades different diodes and a 2D image can be formed by combining successive readings of the detector array. The state of the photo-diodes are conventionally single bit (shaded or not with a threshold at 50%), although newer probes have added as many as three levels of shading. OAPs suffer from several issues. When a particle is not exactly in the object plane of the optical system the recorded image is defocused, resulting in overestimating particle size until the particle is sufficiently defocused so that the detectors do not detect the particle at all. Because the point of defocus depends on particle size, the sample volume of the probe depends on the particle size. However, determining particle concentrations using OAP requires both that the particles are sized correctly and that the sample volume of the particular particle is accurately known. In addition these issues, estimating the size properties of non-spherical particles is problematic with OAPs.

What is needed is a method to estimate a particle size distribution that requires no scattering models or assumptions about the particle properties to relate observed optical signals to particle physical properties. What is also needed is a method to determine the properties of a population of events from an ensemble measurement that has low computational system requirements, does not require extended data collection, and does not include assumptions that cause further uncertainties.

SUMMARY OF THE INVENTION

A method is provided, including the step of obtaining a measured ensemble property distribution function for one or more events. The method further includes the step of generating one or more theoretical ensemble property distribution functions based on Poisson statistics using one or more model parameters. The method further includes the step of determining an event parameter property distribution function by fitting one or more of the theoretical ensemble property distribution functions to the measured ensemble property distribution function using a forward inversion algorithm.

A method is provided including the step of obtaining a measured ensemble particle property distribution function for one or more events using an extinction probe. The method further includes the step of generating one or more theoretical particle property distribution functions based on Poisson statistics using one or more model parameters. The method further includes the step of determining a particle property distribution function by fitting one or more of the theoretical particle property distribution functions to the measured particle property distribution functions using a forward inversion algorithm.

An apparatus is provided including an extinction probe including a light source and a detector, the detector operable to receive the light that passes from the light source through an air sample. The apparatus further includes an electronics operable to determine a measured particle property distribution function for one or more events using the extinction probe, generate one or more theoretical particle property distribution functions based on Poisson statistics using one or more model parameters, and determine a particle property distribution function by fitting one or more of the theoretical particle property distribution functions to the measured particle property distribution function using a forward inversion algorithm.

DETAILED DESCRIPTION OF THE INVENTION

FIGS. 1-6 and the following description depict specific examples to teach those skilled in the art how to make and use the best mode of the Application. For the purpose of teaching inventive principles, some conventional aspects have been simplified or omitted. Those skilled in the art will appreciate variations from these examples that fall within the scope of the Application. Those skilled in the art will appreciate that the features described below can be combined in various ways to form multiple variations of the Application. As a result, the Application is not limited to the specific examples described below, but only by the claims and their equivalents.

Poisson ensemble inversion (PEI) is a technique in which event properties can be inverted, or determined, directly from ensemble measurements instead of measuring individual events and event properties. Ensemble measurements are measurements that may include more than one event at a time, for example detecting more than one particle in a sample of air at a time. PEI inverts data that follows a Poisson distribution, meaning that the one or more events are linear and randomly distributed in a sample space. For example, particle size distributions may be estimated from the particles present in a sample of air, as will be further described below.

Figure 1:
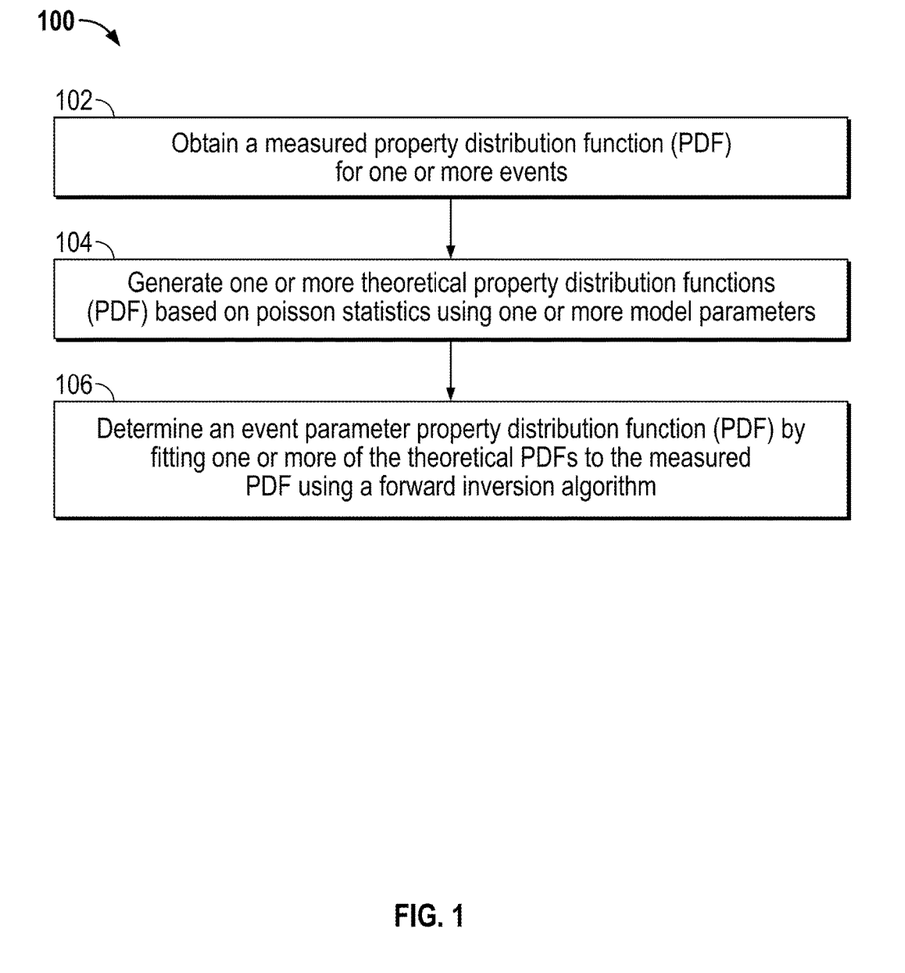
FIG. 1 depicts a method, in accordance with an embodiment.

FIG. 1 depicts a method for determining a distribution of events 100, in accordance with an embodiment. Method 100 begins with step 102. In step 102, a first measured ensemble property distribution function is obtained for one or more events. A property distribution function (PDF) is a histogram, and a measured ensemble PDF is generated from recorded data capturing one or more events. The measured ensemble PDF depicts the frequency that specific events were detected over an interval of time. The event data used to generate the measured ensemble PDF may be obtained using a variety of detectors. For example, in the application of atmospheric sciences, data regarding the presence of particles in an air sample may be received from an extinction probe, a backscattered light detector, or a polarization detector, in addition to others. In the example application of network traffic monitoring, a network traffic analyzer may provide data regarding the presence of data packets. Other applications of obtaining a measured ensemble PDF are also possible using data acquired from other detectors, however, as will be understood by those of skill in the art.

Figure 2:
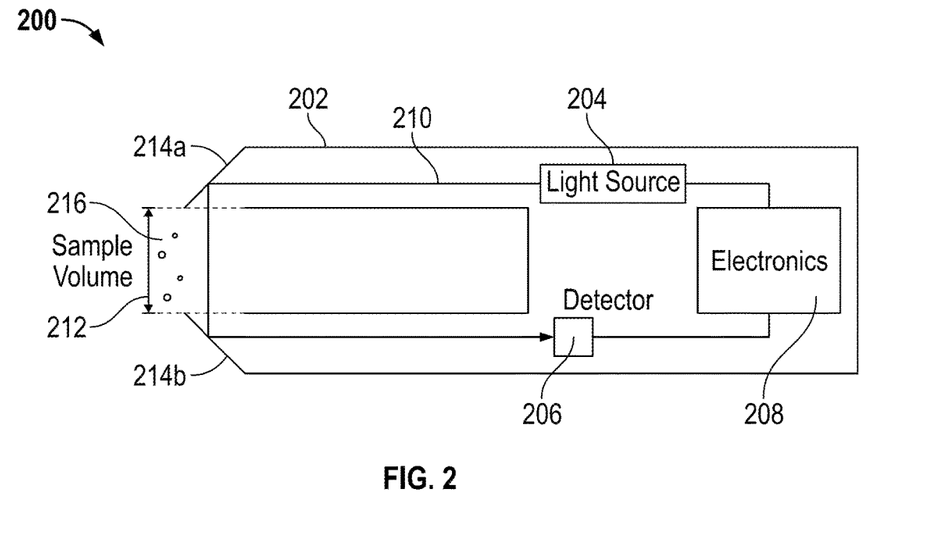
FIG. 2 depicts an extinction probe, in accordance with an embodiment.

In embodiments, the first measured ensemble PDF may be obtained from an extinction probe. FIG. 2 depicts a high-level diagram of an example extinction probe 200. Extinction probe 200 is operable to determine how much a light source is attenuated when the light is obstructed by particles present in an air sample. In embodiments, extinction probe 200 may be placed on any moving or stationary body, including an aircraft, a drone, a surface weather station, or any other platform. Ambient air typically flowed through extinction probe 200 and sampled.

Extinction probe 200 includes a housing 202, a light source 204, a detector 206, and an electronics 208. Light source 204 is operable to produce a light ray 210 inside housing 202. In embodiments, light source 204 may be a laser light source. Light ray 210 may take a path through housing 202 that passes through a sample volume 212 in route to detector 206. Sample volume 212 is a fixed space through which sample air may flow. In embodiments, extinction probe 200 may include further optical elements to manipulate the path of light ray 210, as will be understood by those of skill in the art. For example, extinction probe 200 may include mirrors 214a and 214b.

Extinction probe 200 may be used to determine a first measured ensemble PDF for one or more events. Light ray 210 passes through sample volume 212 and subsequently illuminates detector 206. Airborne particles 216 present in sample volume 212 obstruct or extinguish an amount of light ray 210 proportional to their projected surface areas or cross sectional areas. When multiple particles 216 are detected at once, light ray 210 will be extinguished proportional to the combined projected surface areas of the particles 216. Detector 206 is periodically sampled over predefined time intervals, and the detector 206 power recorded is processed to form the first measured ensemble PDF.

In embodiments, the first measured ensemble PDF may be obtained using any other detector capable of obtaining ensemble event measurements known to those of skill in the art either during a defined interval of time, or during a defined integration period.

Method 100 continues with step 104. In step 104, one or more first theoretical ensemble property distribution functions (PDF) are generated based on Poisson statistics using one or more model parameters. Poisson statistics require that events are linear, occur randomly, and are randomly distributed in the sample space. By linear, what is meant is that each event occurs independently of every other event. Model parameters may include particular events, event property values, or expected values of an event property values. Under Poisson statistics, there is some probability that no events, one event, two events, and so forth will occur in the sample space.

Figure 3:
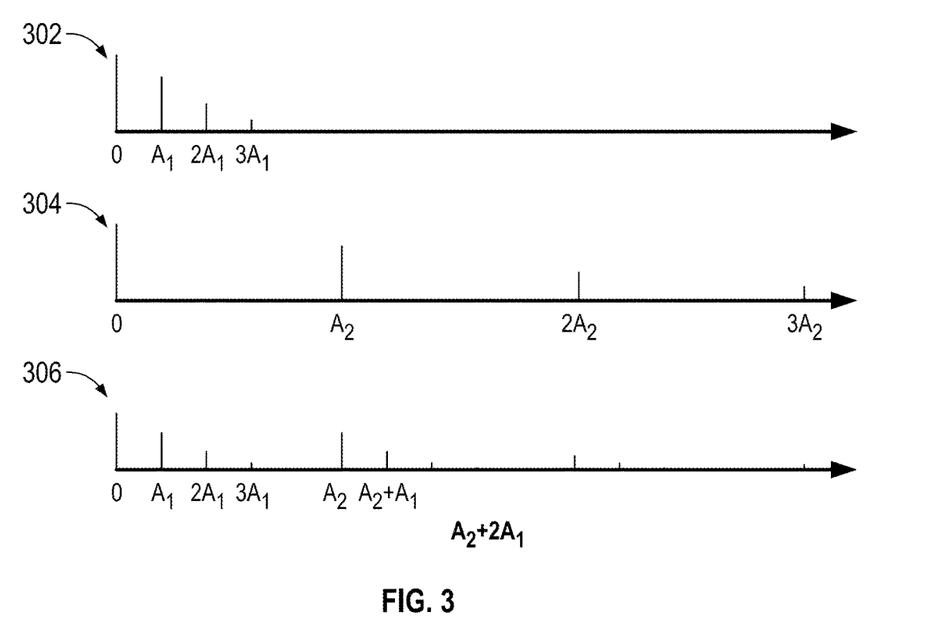
FIG. 3 depicts three property distribution functions, in accordance with an embodiment.

For example, FIG. 3 depicts theoretical ensemble PDFs 302 and 304, in addition to theoretical ensemble PDF 306. Each of theoretical ensemble PDF 302, theoretical ensemble PDF 304, and theoretical ensemble PDF 306 depict a respective distribution of events based upon one or more model parameters, with the x-axis representing event properties and the y-axis representing the probability of observing an event property.

In theoretical ensemble PDF 302, one event type is depicted with the event property value $A_1$. Two events that occur concurrently are represented by event property value $2A_1$, and three events that concurrently occur are represented by event property value $3A_1$, etc. Theoretical ensemble PDF 304 depicts a second event that has the event property value $A_2$ which is not equal to $A_1$. In embodiments, theoretical ensemble PDFs 302 and 304 may be Poisson distributions.

A theoretical ensemble PDF may be built to represent a distribution of multiple linear events based on an ensemble of events exhibiting respective event property values. The theoretical ensemble PDF for multiple linear events is therefore the convolution of the first event theoretical ensemble PDF with the second event theoretical ensemble PDF. This produces a new theoretical ensemble PDF for the combined events which is unique from the first two and depends on the relative number concentrations of the constituent events. For example, events having event property values $A_1$ and $A_2$ may exist in different linear combinations to create expanded theoretical ensemble PDFs from those represented in theoretical ensemble PDF 302 and theoretical ensemble PDF 304. Theoretical ensemble PDF 306 depicts an example mixed population of events where event property values $A_1$ and $A_2$ make one possible relative contribution to theoretical ensemble PDF 306.

In embodiments, a series of theoretical ensemble PDFs may be generated using a range of model parameters. For example, the series of theoretical ensemble PDFs may include a variety of events in a variety of relative contributions.

Method 100 continues with step 106. In step 106, an event parameter property distribution function (PDF) is determined by fitting one or more of the first theoretical ensemble PDFs to the first measured ensemble PDF using a forward inversion algorithm. Once a theoretical model based on Poisson statistics is built in step 104, the theoretical ensemble PDFs may be fit to the measured ensemble PDF using a forward inversion algorithm. The one or more theoretical ensemble PDFs that fit the measured ensemble PDF best are used to determine the parameter PDF. The parameter PDF is an estimate of the actual properties of the measured particle population. In embodiments, the parameter PDF may include the model parameters.

Figure 4:
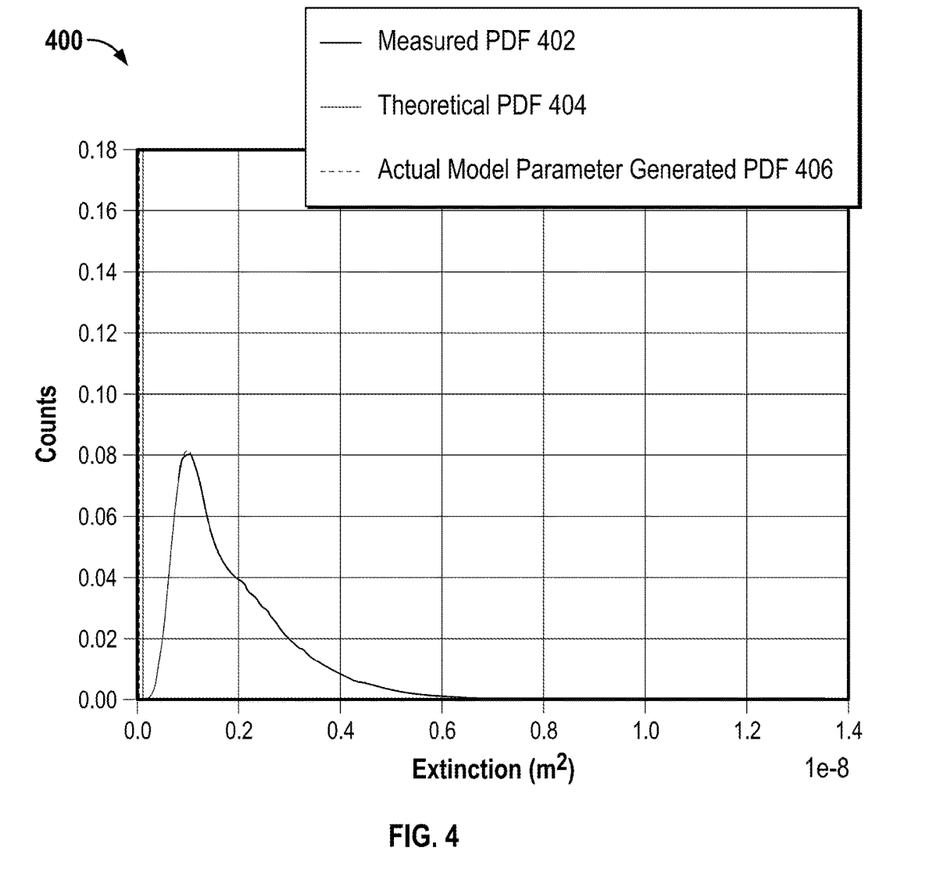
FIG. 4 depicts a measured ensemble property distribution function, in accordance with an embodiment.

FIG. 4 depicts simulation example 400. Simulation example 400 includes a measured ensemble PDF 402, a theoretical ensemble PDF 404, and an actual model parameter generated PDF 406. The x-axis of simulation example 400 represents extinction as measured by an extinction probe, and the y-axis represents the number of counts for a particular extinction example. Measured ensemble PDF 402 represents a Monte Carlo simulated measured ensemble PDF representing particle extinction data. Measured ensemble PDF 402 depicts extinction retrievals that may be obtained with extinction probe 200 for a population of airborne particles 216 that are randomly distributed in sample volume 212. Theoretical ensemble PDF 404 represents the theoretical ensemble PDF determined to have the best fit to measured ensemble PDF 402 using method 100. It may be seen from FIG. 4 that theoretical ensemble PDF 404 is a good approximation of measured ensemble PDF 402 because measured ensemble PDF 402 and theoretical ensemble PDF 404 are substantially identical. Theoretical ensemble PDF 404 was generated by producing a Poisson distribution with model parameters that represent the best-fit to measured ensemble PDF 402. The model parameters in the example of simulation example 400 include a theoretical particle size distribution.

Simulation example 400 further includes actual model parameter generated PDF 406. Actual model parameter generated PDF 406 is a theoretical Poisson distribution generated using the exact model parameter particle distribution that was used in the Monte Carlo simulation that produced measured ensemble PDF 402. Theoretical ensemble PDF 404 has no knowledge of actual model parameter generated PDF 406 because measured ensemble PDF 402 and actual model parameter 406 are generated using different simulations. However, measured ensemble PDF 402, theoretical ensemble PDF 404, and actual model parameter generated PDF 406 are substantially identical, demonstrating the effectiveness of method 100.

Figure 5:
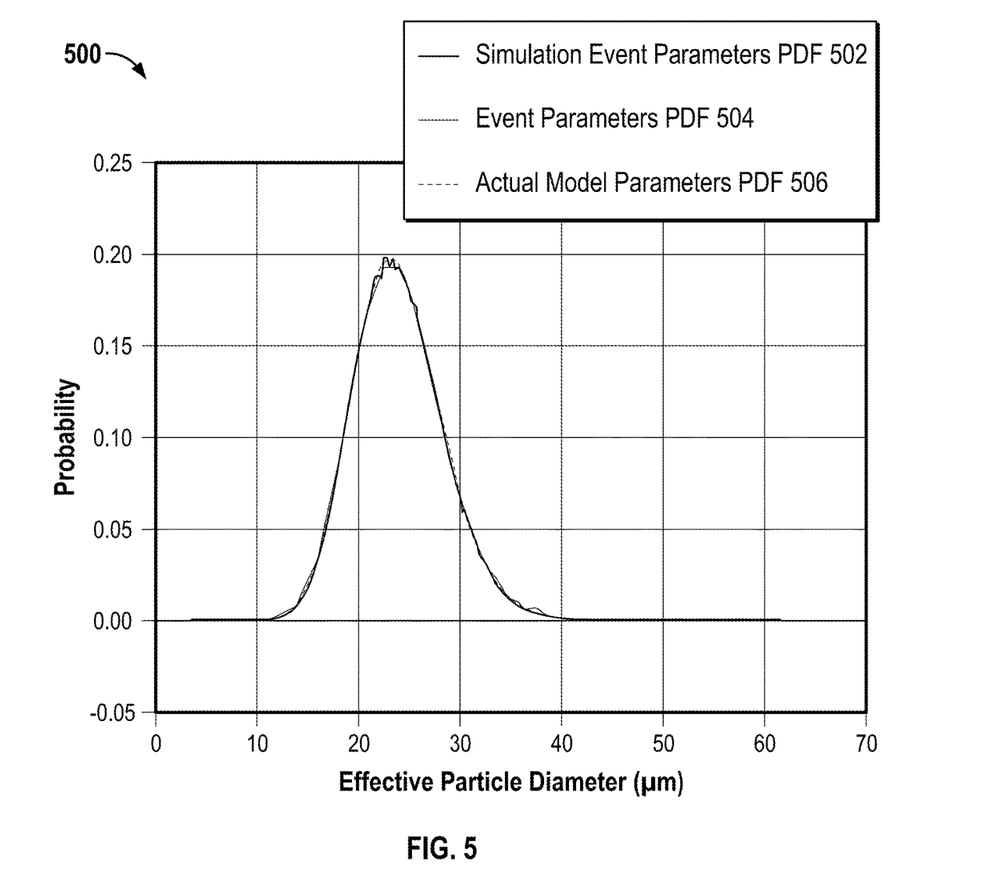
FIG. 5 depicts a particle property distribution function, in accordance with an embodiment.

FIG. 5 further depicts simulation example 500. Simulation example 500 includes three example particle size distributions, including simulation event parameters PDF 502, event parameters PDF 504, and actual model parameters PDF 506. The x-axis of simulation example 500 represents effective particle diameter, and the y-axis represents probability. Simulation event parameters PDF 502 include the event parameters that were simulated via a Monte Carlo simulation of particle size distributions to produce measured ensemble PDF 402. Event parameters PDF 504 represents the particle distribution determined from performing a fit to measured ensemble PDF 402. It may be seen in FIG. 5 that simulation event parameters PDF 502 and event parameters PDF 504 are substantially identical, indicating an effective fit to the data.

Simulation example 500 further includes actual model parameters PDF 506. Actual model parameters PDF 506 includes the actual model parameters used to generate measured ensemble PDF 402. It may be seen in FIG. 5 that simulation event parameter PDF 502, event parameters PDF 504, and actual model parameters PDF 506 are substantially identical. The results of simulation examples 400 and 500 demonstrate that method 100 can accurately reproduce a particle size PDF from extinction measurements.

Figure 6:
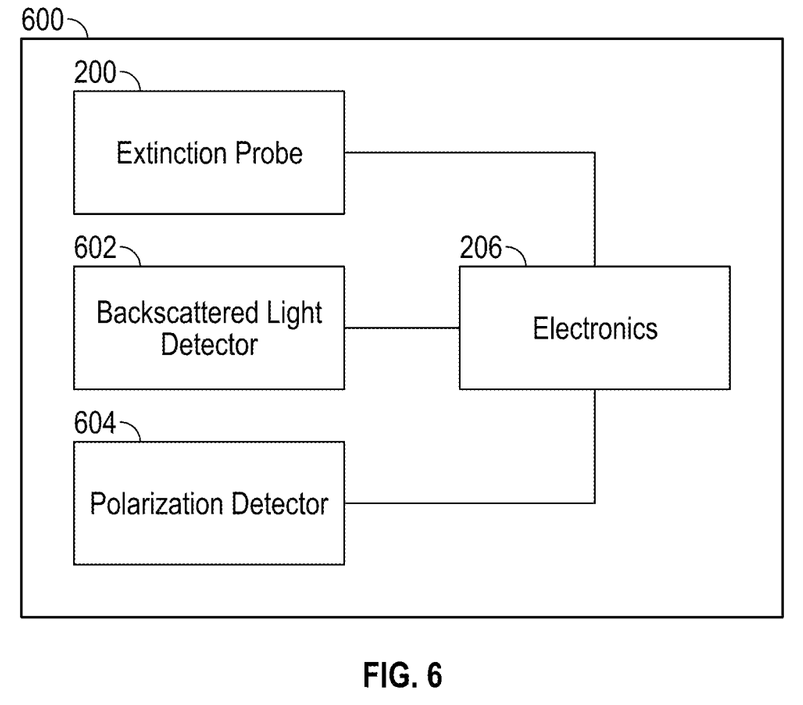
FIG. 6 depicts an apparatus for generating particle property distribution functions, in accordance with an embodiment.

In embodiments, method 100 may be performed on PDF generating system 600. FIG. 6 depicts a high-level block diagram of system 600. In embodiments, system 600 may include any combination of extinction probe 200, backscattered light detector 602, and polarization detector 604. System 600 may further include electronics 206. Backscattered light detector 602 may be used to determine particle composition by detecting the backscattered light proportional to the projected cross sectional areas of airborne particles in a sample volume. Polarization detector 604 may detect particle shape properties of airborne particles. In embodiments, extinction probe 200, backscattered light detector 602, and polarization detector 604 may determine related optical characteristics for a substantially concurrent group of particles.

Electronics 206 is a processing system or computer having a processor, a memory, and electronic interfaces to further electronic devices. Electronics 206 may be operable to send commands to or receive data from extinction probe 200, backscattered light detector 602, polarization detector 604. Electronics 206 may also be operable to perform any of steps the described with regards to method 100.

In embodiments, system 600 may include and/or use any combination of extinction probe 200, backscattered light detector 602, polarization detector 604, and electronics 208 to obtain data and provide measured ensemble PDFs. Extinction probe 200, backscattered light detector 602, and polarization detector 604 may be operated concurrently or sequentially upon substantially the same or different samples of air. Extinction probe 200, backscattered light detector 602, polarization detector 604, and electronics 208 may further be separate or closely integrated together within system 600.

In embodiments, the measured ensemble PDF, the one or more theoretical ensemble PDFs, and the event parameter property PDF may be n-dimensional property distribution functions. For example, the measured ensemble PDF, the theoretical ensemble PDFs, and the event parameter property PDFs may each be a two-dimensional histogram including data from the same two of: extinction probe 200, backscattered light detector 602, and polarization detector 604. Obtaining the measured ensemble PDF in step 102 may include substantially concurrently collecting data from the two detectors, then generating a two-dimensional ensemble PDF with a dimension for the first detector data values, a dimension for the second detector data values, and a third dimension for the number of instances of each pair of first and second detector data values. The theoretical ensemble PDF may be generated in step 104 with the same structure as the measured ensemble PDF. The event parameter PDF, also a two-dimensional histogram, would then be generated by fitting the two-dimensional theoretical ensemble PDFs to the measured ensemble PDF, as described in step 106.

Advantageously, the one or more event parameter PDFs produced using method 100 may be used to monitor optically large, or Geometric regime particle features in a fluid environment or onboard a moving platform. For example, method 100 may be used in a cloud probe to provide estimations of distributions of liquid droplet or ice crystal sizes, shapes, and polarizations in clouds. Method 100 requires minimal processing, shorter data collection times, and fewer assumptions than prior techniques.

While this Application has primarily discussed applications in atmospheric science, this is by no means intended to be limiting. The method may be applied to determine the properties of any ensemble events that behave substantially according to Poisson statistics. For example, method 100 may be applied to estimating the properties of data packets in network traffic.

The detailed descriptions of the above embodiments are not exhaustive descriptions of all embodiments contemplated by the inventors to be within the scope of the Application. Indeed, persons skilled in the art will recognize that certain elements of the above-described embodiments may variously be combined or eliminated to create further embodiments, and such further embodiments fall within the scope and teachings of the Application. It will also be apparent to those of ordinary skill in the art that the above-described embodiments may be combined in whole or in part to create additional embodiments within the scope and teachings of the Application.

I claim:

1. An apparatus comprising:
a property distribution function (PDF) generating system comprising electronics; and
an extinction probe including a housing, one or more mirrors, a light source and a detector, the detector configured to receive light that passes from the light source through an air sample;
wherein the electronics are configured to determine a measured particle property distribution function (PDF) for one or more events using the extinction probe, generate one or more theoretical ensemble property distribution functions (PDF) based on Poisson statistics using one or more model parameters using the PDF generating system, and determine an event parameter property distribution function (PDF) by data fitting one or more of the theoretical ensemble PDFs to the measured particle PDF, wherein the one or more theoretical ensemble PDFs include at least one or more random distributions;
wherein the detector and the light source are within the hosing and a path of the light is manipulated by the mirrors.

2. The apparatus of claim 1, wherein the measured particle PDF further includes data obtained using a second instrument, and the measured particle PDF, the one or more theoretical ensemble PDFs, and the event parameter PDF are each two-dimensional property distribution functions.

3. The apparatus of claim 2, further comprising:
a backscattered light detector;
wherein the measured particle PDF includes data received from the backscattered light detector.

4. The apparatus of claim 1, further comprising:
a polarization detector;
wherein the measured particle PDF includes data received from the polarization detector.

5. The method of claim 1, wherein the measured ensemble PDF records one or more linear and independent events.

6. The method of claim 1, wherein the measured ensemble PDF includes one or more events that are randomly distributed in a sample space.

7. The method of claim 1, wherein the measured ensemble PDF includes events that are obtained during a defined interval of time.

8. The method of claim 1, wherein the measured ensemble PDF, the one or more theoretical ensemble PDFs, and the event parameter PDF are each n-dimensional property distribution functions, with n having a value that is greater than one.

9. The method of claim 8, wherein obtaining the measured ensemble PDF includes using n detectors.

* * * * *